(12) United States Patent  (10) Patent No.: US 7,803,947 B2
Sakato et al.  (45) Date of Patent: Sep. 28, 2010

(54) METHOD FOR PRODUCING THIOCARBAMATE DERIVATIVE

(75) Inventors: Mitsuo Sakato, Nerima-ku (JP); Sumio Terada, Nerima-ku (JP); Kenichi Saitoh, Nerima-ku (JP); Tetsuo Watanabe, Nerima-ku (JP)

(73) Assignee: Zenyaku Kogyo Kabushikikaisha, Tokyo (JP)

( * ) Notice: Subject to any disclaimer, the term of this patent is extended or adjusted under 35 U.S.C. 154(b) by 760 days.

(21) Appl. No.: 11/721,268

(22) PCT Filed: Dec. 9, 2005

(86) PCT No.: PCT/JP2005/022689

§ 371 (c)(1),
(2), (4) Date: Jun. 8, 2007

(87) PCT Pub. No.: WO2006/062201

PCT Pub. Date: Jun. 15, 2006

(65) Prior Publication Data

US 2009/0247762 A1 Oct. 1, 2009

(30) Foreign Application Priority Data

Dec. 10, 2004 (JP) .............................. 2004-358847

(51) Int. Cl.
*C07D 213/72* (2006.01)
(52) U.S. Cl. .................................... 546/297
(58) Field of Classification Search ........................ None
See application file for complete search history.

(56) References Cited

U.S. PATENT DOCUMENTS 2,139,935 A  12/1938  Jean Claudin et al.

FOREIGN PATENT DOCUMENTS

| JP | 59 51265 | 3/1984 |
| JP | 62 48667 | 3/1987 |
| JP | 62 61967 | 3/1987 |

*Primary Examiner*—Zinna N Davis
(74) *Attorney, Agent, or Firm*—Oblon, Spivak, McClelland, Maier & Neustadt, L.L.P.

(57) ABSTRACT

An O-aryl N-(6-alkoxy-2-pyridyl)-N-alkylthiocarbamate represented by the following formula (I):

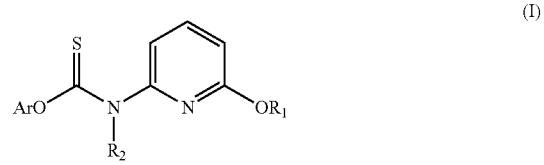

(I)

(wherein $R_1$, $R_2$ and Ar are as defined below) is produced by treating a phenol represented by the following general formula (IV):

$$Ar-OH \quad (IV)$$

(wherein Ar represents an aryl group) with a base in a solvent and then adding thereto an alkali metal salt of N-(6-alkoxy-2-pyridyl)-N-alkyldithiocarbamic acid represented by the following general formula (III):

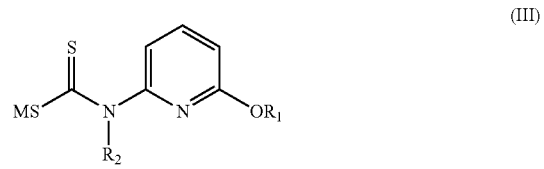

(III)

(wherein $R_1$ and $R_2$ independently represent a $C_1$-$C_4$ alkyl group and M represents an alkali metal) and a halomethane represented by the following general formula (V):

$$CH_2X_mY_n \quad (V)$$

(wherein X and Y represent different halogen atoms, m represents 0, 1 or 2, n represents 0, 1 or 2, and m+n equals 2) for causing a reaction.

8 Claims, No Drawings

METHOD FOR PRODUCING THIOCARBAMATE DERIVATIVE

CROSS REFERENCE TO RELATED APPLICATION

This application is a 371 of PCT/JP05/22689, filed on Dec. 9, 2005, and claims priority to Japanese Patent Application No. 2004-358847, filed on Dec. 10, 2004.

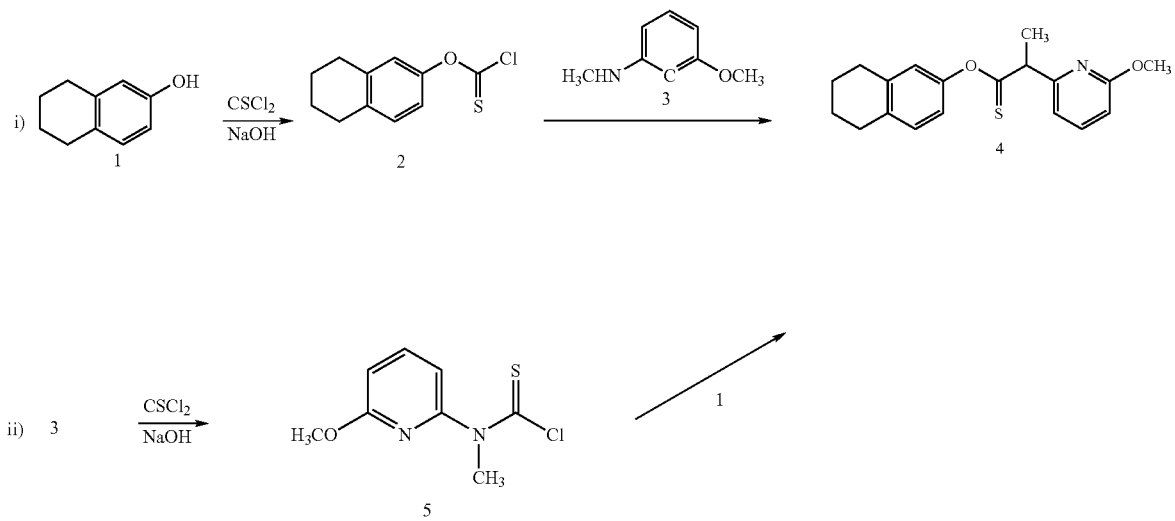

TECHNICAL FIELD

The present invention relates to a method for producing O-aryl N-(6-alkoxy-2-pyridyl)-N-alkylthiocarbamates represented by the general formula (I), which are compounds that are useful as pharmaceuticals such as medications for treating tinea pedis, as agrochemicals such as herbicides, or as intermediaries thereof. In particular, O-(5,6,7,8-tetrahydro-2-naphthyl) N-(6-methoxy-2-pyridyl)-N-methylthiocarbamate is known to be a compound that is useful as a medication for treating tinea pedis.

BACKGROUND ART

Conventional methods of producing O-aryl N-(6-alkoxy-2-pyridyl)-N-alkylthiocarbamates such as the O-(5,6,7,8-tetrahydro-2-naphthyl) N-(6-methoxy-2-pyridyl)-N-methylthiocarbamate indicated by the below Formula (4) have included a method of reacting tetrahydro-2-naphthol (1) with thiophosgene to synthesize tetrahydro-2-naphthylchlorothioformate, then inducing a reaction with 6-methoxy-2-methylaminopyridine (3) as indicated by the reaction scheme i), and a method of reacting 6-methoxy-2-methylaminopyridine (3) and thiophosgene to synthesize N-(6-methoxy-2-pyridyl)-N-methylthiocarbamoyl chloride (5), then inducing a reaction with tetrahydro-2-naphthol (1) as indicated by the reaction scheme ii) (see Patent Document 1)

However, these methods involve the use of thiophosgene, a highly toxic compound which must be produced and used under strictly controlled conditions to ensure the safety of workers, and the transport of which is limited. Therefore, industrial procedures using thiophosgene can be considered to be very inconvenient.

For this reason, various methods not using thiophosgene have been proposed. Among these, methods using carbon disulfide are useful for being safe and cheaply performed (see Patent Document 2 and Patent Document 3).

That is, as indicated by the following reaction scheme iii), a reaction is induced between 6-methoxy-2-methylaminopyridine (3) and carbon disulfide to obtain sodium dithiocarbamate (6), which is then reacted with tetrahydronaphthyl-(2,4-dinitrophenyl) ether (7) to obtain the target compound (4). Alternatively, a reaction is induced between sodium dithiocarbamate (6) and 1-chloro-2,4-dinitrobenzene (8) to obtain a dithiocarbamic acid active ester (9), which is then reacted with tetrahydronaphthol (1) to obtain the target compound (4).

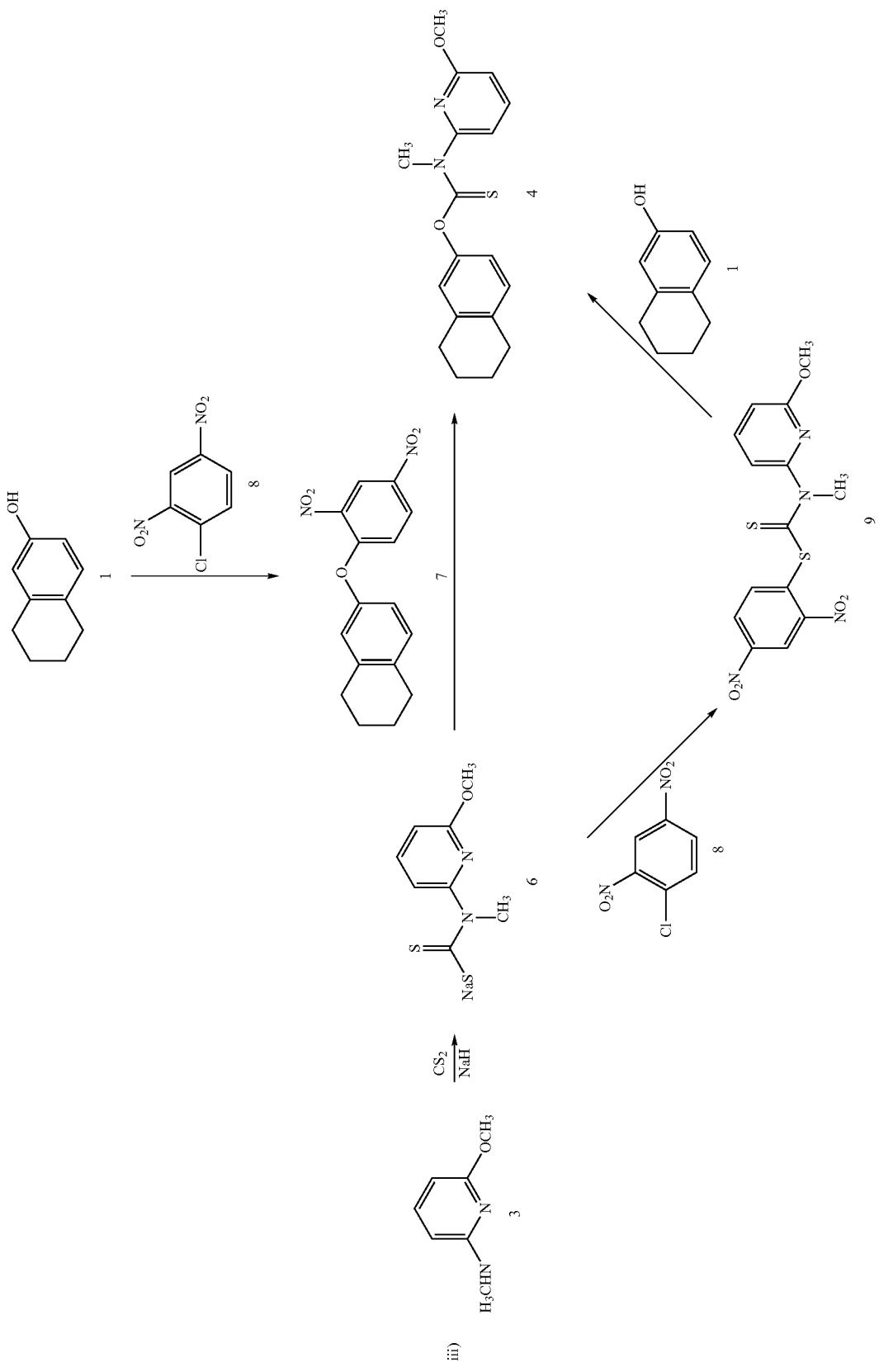

Patent Document 1: JP-B S61-30671

Patent Document 2: JP-B H6-35442

Patent Document 3: P-B H6-74250

DISCLOSURE OF THE INVENTION

Problems to be Solved by the Invention

However, the methods of Patent Document 2 and Patent Document 3 require steps of producing intermediaries (7) and (9) having 2,4-dinitrophenyl as leaving groups. Additionally, upon performing follow-up tests on the methods disclosed in the above patents, not only did they not result in the yields indicated in the patent specifications, they also had poor reproducibility. Additionally, the removal of 2,4-dinitrothiophenol generated after the reaction posed a problem in the final purification step of the target compound.

The present inventors performed diligent research toward improving on the aforementioned draw-backs to achieve a method for safely producing the relevant compound economically and in few steps. As a result, they discovered that whereas a reaction between the alkali metal salt of 6-alkoxy-2-alkylaminopyridine thiocarbamic acid of the below general formula (III) and a phenol of the general formula (IV) does not conventionally progress even after heating to at least 100° C., O-aryl N-(6-alkoxy-2-pyridyl)-N-alkylthiocarbamate can be obtained efficiently in a single step under mild conditions, by adding a halomethane of general formula (V).

Means for Solving the Problems

That is, the present invention offers an industrially advantageous method of producing O-aryl N-(6-alkoxy-2-pyridyl)-N-alkylthiocarbamate, wherein a reaction is induced, in the presence of a halomethane of general formula (V), between a phenoxide obtained by treating a phenol of general formula (IV) with a base in a solvent and an alkali metal salt of N-(6-alkoxy-2-pyridyl)-N-alkyldithiocarbamic acid of general formula (III) obtained by inducing a reaction between the 6-alkoxy-2-alkylaminopyridine of general formula (II) with carbon disulfide in the presence of a base as shown in the below reaction scheme iv), or an alkali metal salt of N-(6-alkoxy-2-pyridyl)-N-alkyldithiocarbamic acid of the above general formula (III) obtained by another method

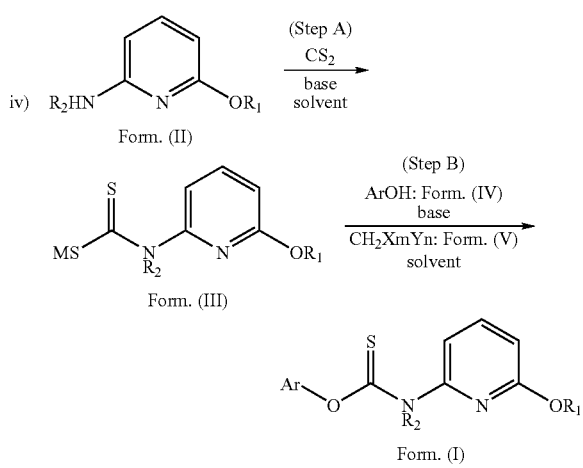

(wherein $R_1$ and $R_2$, independent of each other, denote $C_1$-$C_4$ alkyl groups, Ar denotes an aryl group, M denotes an alkali metal, X and Y denote different halogen atoms, m denotes 0, 1 or 2, n denotes 0, 1 or 2, and m+n=2).

While the production method of the present invention is indicated by the above reaction scheme, the meanings and examples of the terminology used in defining the symbols in the scheme shall be described below.

"$C_1$-$C_4$", when not otherwise restricted, refers to the presence of 1-4 carbon atoms.

Examples of "$C_1$-$C_4$ alkyl groups" include normal or branched alkyl groups such as methyl, ethyl, n-propyl, iso-propyl, n-butyl and tert-butyl, among which methyl is particularly preferable.

Examples of "alkali metals" include sodium, potassium and the like.

Examples of "halogen atoms" include fluorine, chlorine, bromine and iodine.

Examples of "aryl groups" include tetrahydronaphthyl groups, or phenyl groups optionally substituted by a $C_1$-$C_4$ alkyl group.

According to a first method of the present invention, the compound of general formula (III) can be used as the starting material to synthesize the target substance in a single step, and according to a second method of the present invention, the compound of general formula (II) can be used as the starting material to synthesize the target substance in two steps. Additionally, the above second method can be considered to be characterized by selective introduction of the sulfur source of the carbon disulfide as thiocarbonyl groups. Furthermore, the most important characteristic of the present invention is that a carbamate construction reaction, which does not progress when using only the compound of general formula (III), the compound of general formula (IV), a base and a solvent, is caused to progress efficiently with the addition of halomethane.

As the base used for dithiocarbamylation in step A of the present invention, it is possible to use sodium hydride, sodium amide, lithium aluminum hydride, sodium borohydride, lithium amide, lithium hydride, potassium hydride or the like. Good results can be achieved by using 1.0-1.1-fold equiv of both carbon disulfide and the base toward the 6-alkoxy-2-alkylaminopyridine of general formula (II). With a molar ratio of less than 1.0, the yield is poor, and with a molar ratio of more than 1.1, the effects are not improved, and is not economical. As the solvent, it is possible to use ethers such as diethyl ether, tetrahydrofuran (THF) and dioxane, aromatic hydrocarbons such as benzene, toluene and xylene, and polar solvents such as N,N-dimethylformamide (DMF) and dimethylsulfoxide.

The reaction temperature should typically be held within the range of about 0-50° C., preferably in the range of about 5-25° C. If the temperature is too low, the reaction speed is slow, and if the temperature is too high, side reactions can occur, thus reducing the yield. While the alkali metal salt of N-(6-alkoxy-2-pyridyl)-N-alkyldithiocarbamic acid obtained by the reaction can be isolated, it can also be used in the next step without isolation, while still in the reaction solution.

Next, in step B, a reaction is induced between the alkali metal salt of dithiocarbamic acid obtained by the above-described reaction and the phenols, whereby the target substance O-aryl N-6-alkoxy-2-pyridyl)-N-alkylthiocarbamate can be easily produced.

As the phenol, it is possible to use a tetrahydronaphthol or a phenol optionally substituted by a $C_1$-$C_4$ alkyl group as indicated in the definition of Ar in general formula (IV).

Good results can be achieved by using 1.0-1.1 fold equiv of the phenol toward the alkali metal salt of dithiocarbamic acid. With a molar ratio of less than 1.0, the yield is poor, and with a molar ratio of more than 1.1, the effects are not improved, and is not economical.

Before the reaction with the alkali metal salt of N-(6-alkoxy-2-pyridyl)-N-alkyldithiocarbamic acid, the phenols are treated with an equivalent amount of a base to form a phenoxide. The base used in this case may be sodium hydroxide, potassium hydroxide, sodium carbonate, potassium carbonate, sodium hydrogencarbonate, potassium hydrogencarbonate, sodium hydride, lithium hydride, sodium amide or the like, among which sodium hydroxide and potassium hydroxide are preferred. When the phenoxides generated in the reaction system are stable, it is possible to use those that have been produced beforehand.

Additionally, the halomethane used to activate the reaction may be dichloromethane, dibromomethane, diiodomethane, bromochloromethane or the like, among which dichloromethane and diboromethane are preferred for their yields and for economic reasons. The amount of the halomethane used should preferably be 1.0-2.0 fold equiv. of the alkali metal salt of dithiocarbamic acid, and the use of any more does not result in any improvement in yield.

While the reaction solvent may be DMF, N,N-dimethylacetamide, dimethylsulfoxide, pyridine, quinoline, or a mixture thereof, DMF is particularly preferred.

Since the reaction is exothermic, the reaction temperature should preferably be held to within the range of about 10-50° C. If the temperature is too low, the reaction rate is slow, and if the temperature is too high, side reactions can occur, thus reducing the yield.

The 6-alkoxy-2-alkylaminopyridine of general formula (II) which is the starting material of the present invention is a compound that is generally known through publications, easily producible by reacting 2,6-dichloropyridine with alkylamine, then with an alcohol in the presence of a base, and also available as a commercial product.

On the other hand, the present invention is not restricted to the above embodiment, and the O-aryl N-6-alkoxy-2-pyridyl)-N-alkylthiocarbamate represented by the general formula (I) can be efficiently produced as described above, even when using an alkali metal salt of N-(6-alkoxy-2-pyridyl)-N-alkyldithiocarbamic acid obtained by a method other than step A of the reaction scheme iv).

EFFECTS OF THE INVENTION

The method of the present invention adds a new step of using a phenol, a base and a halomethane with an alkali metal salt of dithiocarbamic acid, instead of using the highly toxic thiophosgene, as a sulfur source, in the production of O-aryl N-(6-alkoxy-2-pyridyl)-N-alkylthiocarbamate which is useful as a pharmaceutical, an agrochemical or an intermediary thereof, thereby offering a method of production that is safer and has fewer steps than conventional production methods. The invention is particularly characterized by the discovery that a reaction that does not conventionally progress can be made to progress efficiently under mild conditions with the use of a halomethane.

BEST MODES FOR CARRYING OUT THE INVENTION

Next, the present invention will be described in detail with reference to examples, but the present invention is not to be construed as being restricted to these examples.

Example 1

1) Production of sodium 6-methoxy-2-methylaminopyridine dithiocarbamate 6-methoxy-2-methylaminopyridine (25.6 g, 0.185 mol) was dissolved in 120 ml of dehydrated THF, and 60% sodium hydride (7.4 g, 0.185 mol) was added. This was then refluxed for 1 hour, and upon becoming transparent, allowed to cool to room temperature. Carbon disulfide (14.1 g, 0.185 mol) was added dropwise into this solution, which was then stirred for two hours at room temperature. 300 ml of hexane were added and stirring continued until crystals precipitated out. The precipitated crystals were filtered out, then washed with 200 ml of hexane, and dried overnight in a dessicator to obtain 43.6 g (yield 99.7%) of the titled compound in the form of a pale yellow powder.

2) Production of O-(5,6,7,8-tetrahydro-2-naphthyl) N-(6-methoxy-2-pyridyl)-N-methylthiocarbamate 5,6,7,8-tetrahydro-2-naphthol (1.48 g, 10 mmol) was dissolved in 10 ml of DMF, after which crushed sodium hydroxide (0.60 g, 15 mmol) was added, then stirred for 10 minutes at room temperature. Next, sodium 6-methoxy-2-methylaminopyridine dithiocarbamate (2.36 g, 10 mmol) was added and the result stirred for 10 minutes. The solution was ice-cooled to 10° C., and dibromomethane (1.74 g, 10 mmol) was added dropwise for 5 minutes, and stirred for 1 hour at room temperature. 100 ml of ethyl acetate were added to the reaction solution to extract, and the organic layer was washed with water. The organic layer was dried with anhydrous magnesium sulfate, then the magnesium sulfate was filtered out. Upon concentrating the filtrate under reduced pressure, an oily residue was obtained. This was purified by column chromatography (hexane:ethyl acetate=20:1), to obtain 1.91 g (yield 58%) of the titled compound in the form of colorless crystals.

Melting Point: 99-100° C.

NMR (CDCl$_3$) δ (ppm): 1.77 (4H, bs), 2.75 (4H, bs), 3.75 (3H, s), 3.93 (3H, s), 6.65 (1H, d, J=8.0 Hz), 6.78-7.08 (4H, m), 7.64 (1H, t, J=8.0 Hz)

IR (KBr) cm$^{-1}$: 1603, 1460, 1413, 1369, 1325, 1262, 1175, 1035, 808, 785

MS m/z: 328 (M$^+$)

Examples 2-9

Various O-aryl N-(6-alkoxy-2-pyridyl)-N-alkylthiocarbamates were obtained by inducing reactions with the sodium 6-methoxy-2-methylaminopyridine dithiocarbamate produced in the above Example 1, 1) (step A) under the same conditions as in the above-described Examples 1, 2) and 2) aside from the fact that the phenols of general formula (IV), halomethanes of general formula (V) and bases used in the above Example 1, 2) (step B) were changed as shown in Table 1. The spectral data etc. of the resulting compounds are shown below.

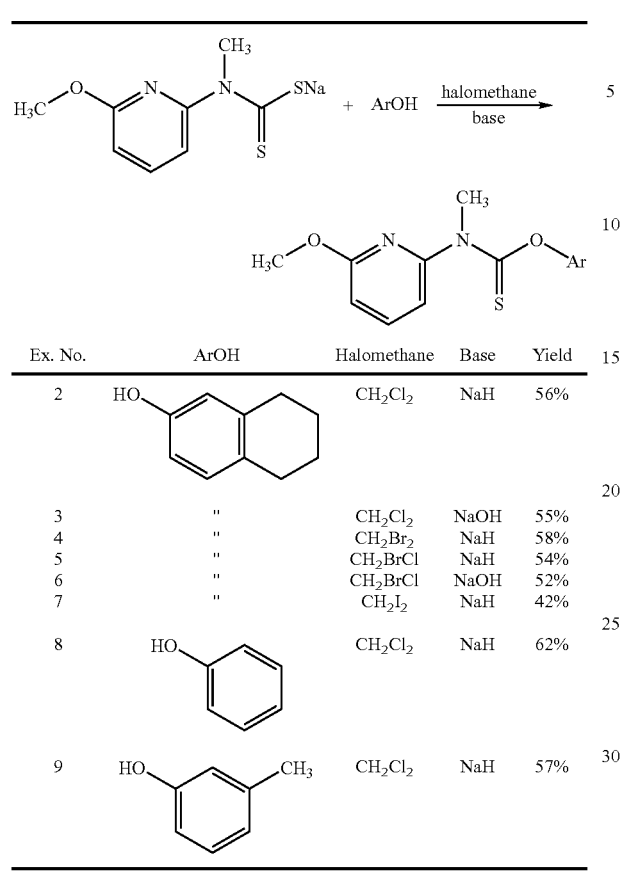

| Ex. No. | ArOH | Halomethane | Base | Yield |
|---|---|---|---|---|
| 2 | 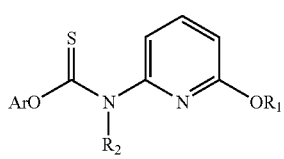 | $CH_2Cl_2$ | NaH | 56% |
| 3 | " | $CH_2Cl_2$ | NaOH | 55% |
| 4 | " | $CH_2Br_2$ | NaH | 58% |
| 5 | " | $CH_2BrCl$ | NaH | 54% |
| 6 | " | $CH_2BrCl$ | NaOH | 52% |
| 7 | " | $CH_2I_2$ | NaH | 42% |
| 8 | HO-C₆H₅ | $CH_2Cl_2$ | NaH | 62% |
| 9 | HO-C₆H₄-CH₃ | $CH_2Cl_2$ | NaH | 57% |

Compound of Example 8

Melting Point: 79-81° C.

NMR (CDCl$_3$) δ (ppm): 3.76 (3H, s), 3.94 (3H, s), 6.67 (1H, d, J=8 Hz), 7.01-7.10 (3H, m) 7.22-7.25 (1H, m), 7.25-7.27 (2H, m), 7.62 (1H, t, J=8 Hz)

IR (KBr) cm$^{-1}$: 1605, 1463, 1414, 1369, 1328, 1265, 1171, 1018, 792, 771, 688

MS m/z: 274 (M$^+$)

Compound of Example 9

Melting Point: (oil)

NMR (CDCl$_3$) δ (ppm): 2.30 (3H, s), 3.76 (3H, s), 3.94 (3H, s), 6.90 (1H, br), 7.00 (1H, t, J=8 Hz), 7.04 (1H, d, J=8 Hz), 7.03 (2H, t, J=8 Hz), 7.25 (1H, t, J=8 Hz), 7.61 (1H, t, J=8 Hz)

IR (KBr) cm$^{-1}$: 160, 1463, 1412, 1364, 1327, 1265, 1178, 1026, 783

MS m/z: 288 (M$^+$)

The invention claimed is:

1. A method of producing an O-aryl N-(6-alkoxy-2-pyridyl)-N-alkylthiocarbamate represented by formula (I):

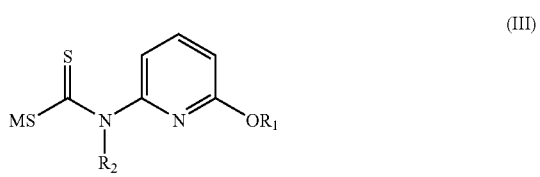

(wherein R$_1$ and R$_2$, independent of each other, denote C$_1$-C$_4$ alkyl groups and Ar denotes an aryl group), comprising treating a phenol represented by formula (IV):

Ar—OH      (IV)

(wherein Ar is as defined above) with a base in a solvent, adding thereto an alkali metal salt of N-(6-alkoxy-2-pyridyl)-N-alkyldithiocarbamic acid represented by formula (III):

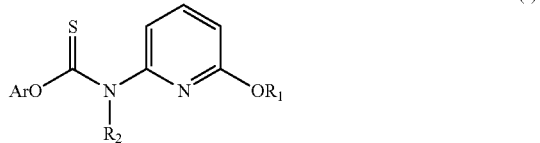

(wherein R$_1$ and R$_2$ are as defined above, and M denotes an alkali metal) and a halomethane represented by formula (V):

$$CH_2X_mY_n \qquad (V)$$

(wherein X and Y denote different halogen atoms, m denotes 0, 1 or 2, n denotes 0, 1 or 2, and m+n=2), and allowing to react to produce said O-aryl N-(6-alkoxy-2-pyridyl)-N-alkylthiocarbamate represented by formula (I).

2. A method of producing an O-aryl N-(6-alkoxy-2-pyridyl)-N-alkylthiocarbamate represented by formula (I):

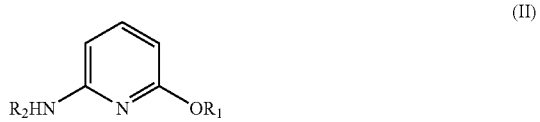

(wherein R$_1$ and R$_2$, independent of each other, denote C$_1$-C$_4$ alkyl groups and Ar denotes an aryl group), comprising:

causing a 6-alkoxy-2-alkylaminopyridine represented by formula (II):

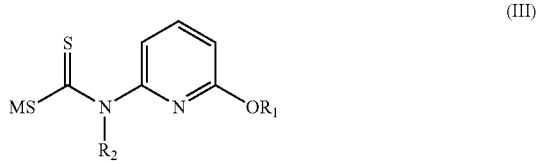

(wherein R$_1$ and R$_2$ are as defined above) to react with carbon disulfide in the presence of a base, to produce an alkali metal salt of N-(6-alkoxy-2-pyridyl)-N-alkyldithiocarbamic acid represented by formula (III):

(wherein $R_1$ and $R_2$ are as defined above, and M denotes an alkali metal); and treating a phenol represented by formula (IV):

$$Ar-OH \quad (IV)$$

(wherein Ar is as defined above) with a base in a solvent, adding thereto said alkali metal salt of N-(6-alkoxy-2-pyridyl)-N-alkyldithiocarbamic acid represented by formula (III) and a halomethane represented by formula (V):

$$CH_2X_mY_n \quad (V)$$

(wherein X and Y denote different halogen atoms, m denotes 0, 1 or 2, n denotes 0, 1 or 2, and m+n=2), and allowing to react to produce said O-aryl N-(6-alkoxy-2-pyridyl)-N-alkylthiocarbamate represented by formula (I).

3. A method in accordance with claim 1 or 2, wherein $R_1$ and $R_2$ are both methyl groups.

4. A method in accordance with claim 1 or 2, wherein Ar is a tetrahydronaphthyl group, or a phenyl group optionally substituted by a $C_1$-$C_4$ alkyl group.

5. A method in accordance with claim 1 or 2, wherein M is sodium.

6. A method in accordance with claim 1 or claim 2, wherein the halomethane of formula (V) is $CH_2Cl_2$, $CH_2Br_2$, $CH_2I_2$ or $CH_2BrCl$.

7. A method in accordance with claim 2, wherein the base in step A is sodium hydride.

8. A method in accordance with claim 1 or claim 2, wherein the solvent used in the reaction from the alkali metal salt of dithiocarbamic acid represented by formula (III) to the compound represented by formula (I) is N,N-dimethylformamide.

* * * * *